(12) United States Patent  (10) Patent No.: US 7,100,424 B2
Wilson  (45) Date of Patent: Sep. 5, 2006

(54) APPARATUS FOR ACCESSING CONTAINER SECURITY THREATS AND METHOD OF USE

(76) Inventor: Marshall Wilson, 1737 Milford, Houston, TX (US) 77098

( * ) Notice: Subject to any disclaimer, the term of this patent is extended or adjusted under 35 U.S.C. 154(b) by 0 days.

(21) Appl. No.: 10/896,397

(22) Filed: Jul. 22, 2004

(65) Prior Publication Data

US 2006/0169025 A1    Aug. 3, 2006

(51) Int. Cl.
G01N 1/24 (2006.01)
G01N 1/26 (2006.01)
G01N 31/00 (2006.01)

(52) U.S. Cl. ............... 73/31.05; 73/31.02; 73/31.03; 73/863; 73/863.33; 73/863.83; 73/864.34

(58) Field of Classification Search ............ 73/31.01, 73/31.02, 31.03, 31.05, 863, 863.81, 863.83, 73/864.34, 863.33; 701/2; 901/1, 46
See application file for complete search history.

(56) References Cited

U.S. PATENT DOCUMENTS

| | | | |
|---|---|---|---|
| H1293 H * | 3/1994 | Carlon | 73/23.2 |
| 5,440,916 A * | 8/1995 | Stone et al. | 73/23.31 |
| 5,443,354 A * | 8/1995 | Stone et al. | 414/729 |
| 5,638,420 A | 6/1997 | Armistead | |
| 5,838,759 A | 11/1998 | Armistead | |
| 5,859,362 A * | 1/1999 | Neudorfl et al. | 73/23.2 |
| 6,047,588 A | 4/2000 | Danilychev | |
| 6,234,006 B1 * | 5/2001 | Sunshine et al. | 73/29.01 |
| 6,344,818 B1 | 2/2002 | Markov | |
| 6,637,277 B1 * | 10/2003 | Gamache et al. | 73/863.33 |
| 6,658,087 B1 | 12/2003 | Chalmers | |
| 6,701,772 B1 * | 3/2004 | Kreichauf et al. | 73/23.2 |
| 6,909,907 B1 * | 6/2005 | Oyang et al. | 455/556.1 |
| 2003/0108150 A1 | 6/2003 | Franke | |
| 2003/0201394 A1 | 10/2003 | Peoples | 250/336.1 |
| 2004/0020267 A1 | 2/2004 | Megerle | 73/31.03 |

OTHER PUBLICATIONS

Williams, A. "Trace Chemical Mine Detection Data Collection Final Scientific and Technical Report" Sep. 15, 2003, pp. 1-102.*

* cited by examiner

Primary Examiner—Daniel S. Larkin

(57) ABSTRACT

A system and method for accessing the security threat of a cargo container by sampling the air contained therein. The system is capable of analyzing the air disposed within the container for security threats including chemical, biological, radiological, nuclear, and high explosive threats, as well as other types of contraband such as illegal substances, embargoed material or stowaways, without requiring the modification of the existing container, the movement of the container to a particular inspection site, and without opening the container. The system generally includes a detection system comprising a detector array, an air-moving device, and one or more air-sampling devices. The entire system is mounted upon a vehicle for mobility.

17 Claims, 4 Drawing Sheets

APPARATUS FOR ACCESSING CONTAINER SECURITY THREATS AND METHOD OF USE

STATEMENT REGARDING FEDERALLY SPONSORED RESEARCH OR DEVELOPMENT

Not Applicable

FIELD OF THE INVENTION

The present invention relates to an apparatus for assessing the security threat of a cargo container by sampling the air contained therein. More specifically, it relates to a device for the inspection of an individual cargo container that is capable of analyzing the air disposed within the container for security threats including chemical, biological, radiological, nuclear, and high-explosive threats without requiring the modification of the existing container, the movement of the container to a particular inspection site, and without opening the container. In addition, the present invention could also be used to detect other types of contraband, including illegal substances, embargoed materials and stowaways.

BACKGROUND OF THE INVENTION

The global economy depends upon the physical shipment of materials between markets. The scale and pace at which these materials are shipped has exploded in recent years due in part to the invention and proliferation of the intermodal container. Ninety percent of the world's freight now moves in a container. Virtually anyone in the world can arrange with an international shipper or carrier to have an empty intermodal container delivered to their home or workplace. They then could load it with tons of material, declare in only the most general terms what the contents were, "seal" it with a 50-cent lead tag, and send it on its way to any city and town in the United States. The job of transportation providers was to move the box as expeditiously as possible and to exercise care to ensure that the integrity of a container's contents was not compromised.

The responsibility for making sure that goods loaded in a container were legitimate and authorized is shouldered almost exclusively by the importing jurisdiction. However, as the volume of containerized cargo has grown, the number of agents assigned to police that cargo has stayed relatively flat or even declined among most trading nations. The rule of thumb in the inspection business is that it takes five agents three hours to conduct a thorough physical examination of a single full intermodal container. Last year nearly 20 million containers were delivered to America's borders via ship, train, and truck. Approximately 1 to 2 percent of that cargo was actually inspected.

Thus, for would-be terrorists, the global intermodal container system that is responsible for moving the overwhelming majority of the world's freight provides ample opportunity for launching a terrorist attack. The almost complete absence of any security oversight in the loading and transporting of a container from its point of origin to its final destination and the growing volume and velocity at which containers move around the planet creates a daunting problem for inspectors. The use of these containers as a weapon has the potential to halt all shipments of containerized cargo into our ports and across our borders. Consequently, a relatively low cost terrorist attack could result in billions of dollars in losses to the U.S. economy.

Given the current state of container security, it is hard to imagine how a post-event lockdown on container shipments could be either prevented or short-lived. A terrorist could easily use a container as a weapon delivery device, for example, high-explosives such as those used in the attack on the Murrah Federal Building in Oklahoma City, some form of chemical weapon, a bio weapon, a nuclear device or "dirty bomb." All these scenarios are conceivable since the choice of a weapon would not be constrained by any security measures currently in place in seaports or within the intermodal transportation industry.

Conventional devices for inspecting containers generally involve the use of penetrating radiation to detect contraband. For example, U.S. Pat. No. 4,430,568 (Osami Yoshida et al.) describes a package inspection system for automatically inspecting the contents of a package, such as a container, unloaded from a ship without opening or unpacking the container. The device comprises an X-ray transmitter, an X-ray receiver, and a processing unit for image processing. This device relies on a large X-ray unit and requires the container be moved through the unit. Similarly, U.S. Pat. No. 5,638,420 (Armistead) describes a radiographic inspection apparatus for large containers, vehicles and structures having a movable frame, which can straddle the container or object being inspected. The straddling frame has opposed parallel sides, which carry a source of penetrating radiation and a detector array. The source or sources are moved along the length of a container while radiographic image data is being sequentially recorded. While this device does not necessarily require the movement of the container to an inspection site, the straddling frame at least requires some space between containers in which to move. Since containers are often stacked in close proximity, the Armistead device would at least require that some containers be moved prior to inspection. Furthermore, neither of the devices described above provide for the actual detection of chemical or biological contaminants, rather they rely on radiation imaging to detect suspect structures or nuclear materials.

Published U.S. Patent Application No. 2003/0201394 (Peoples) describes a device that detects radiological or chemical contaminants in cargo containers via a detector system mounted upon a spreader bar. The device is capable of sampling air next to an existing opening, such as a vent, in the container or inserting an air sampling probe into a spring loaded door located in the roof of the container. The device described by Peoples centers on the rationale that the container being inspected is in the process of being lifted by the spreader bar and is not in close proximity to other containers. Therefore, any contamination detected in the air adjacent to the container is assumed to emanate from the container being lifted. This device would not provide accurate results if the container were in storage and stacked adjacent to other containers. In addition, the spring loaded door requires the modification of the existing container.

Published U.S. Patent Application No. 2004/0024278 (Megerle) describes a device that samples the air of a container for biological and chemical contaminants. The device is directed toward containers having an air distribution plenum that can establish a flow of air through the container, which is then analyzed for the presence of hazardous materials. Similar to the device described in Peoples, this device also requires the modification of the container by installing a means to distribute an air flow through the container. In addition, the Megerle device requires both an air delivery mechanism and an air collection mechanism since the system relies upon a positive pressure source for its air supply.

SUMMARY OF THE INVENTION

The device and method herein disclosed, provides for the inspection of an individual cargo container that is capable of analyzing the air disposed within a container for security threats including chemical, biological, radiological, nuclear, and high-explosive threats. In addition, the present invention could also be used to detect other types of contraband, including illegal substances, embargoed materials, hazardous industrial materials, chemical vapor or material, and human occupancy of the container, such as by sensing carbon dioxide concentration or by auditory means. The device would also be useful for analyzing the air contained within any contained space, such as railroad boxcars, aircraft passenger, cargo, and luggage compartments, liquid cargo containers such as tankcars, tractor trailers, ships, and storage tanks. The device generally comprises a vent cup mounted upon a telescoping actuator. The vent cup is designed to mate with the standard vents installed upon various cargo containers, thus may be manufactured in various shapes and sizes. For example, the vent cup for mating to a standard TC 104 container will be generally rectangular in shape and designed to fit against the vent. Generally, the vent cup comprises an outer shell defining an interior space into which an air sample will be drawn. The outer shell has a leading edge surrounding the interior space that mates with the wall of the container. A seal is disposed along the leading edge to ensure that the air located within the container is drawn into the vent cup. The seal may be manufactured of a rubber, foam, or any suitable pliable and conforming material, so that it conforms to any irregularities in the container wall. Alternatively, the seal may be in the form of an inflatable bladder, which can also conform to the shape of the container wall. The outer shell of the vent cup also comprises an air duct that connects the vent cup to an air-moving device, such as a vacuum pump, air compressor, or similar device, which pulls the air from within the container into the vent cup and through the air duct. If an inflatable bladder is used as the vent cup seal, the air-moving device may comprise a reversible motor such that the air-moving device can be employed to inflate the bladder as necessary. The air duct connecting the vent cup to the air-moving device travels along the length of the telescoping actuator holding the vent cup and terminates at the air-moving device, which discharges into an air distribution manifold. The air distribution manifold is coupled to a detection system, comprising a plurality of individual detectors capable of detecting chemical and high-explosive agents, biological agents, radiological agents, and nuclear material. The entire system is mounted upon a mobile platform, which can be placed within close proximity to a container while the container is in storage or while the container is in place upon the vessel, truck, plane, or railcar on which it was shipped. The mobile platform is also equipped with a control mechanism for extending and retracting the telescoping actuator in order to position the vent cup and seal it against the vent of the container from which the air is to be sampled. The vent cup may also comprise a radiological detection device, such as Geiger counters, ionization detectors, semiconductor diode detectors, scintillation counters, neutron detectors, and the like. In addition, the vent cup may also house any other detector in which proximity to the sample point is important. The system may also comprise a removable, manually telescoping wand that is also connected to the air-moving device. When a wand is employed, the suction port of the air-moving device may be manifolded such that either the wand or the vent cup is selectable as a means to sample the air within a container. The suction end of the wand may be fitted with a crevice tool that can be positioned adjacent to, or inserted into, any opening or crack in the container shell when a vent is inaccessible. Like the air duct of the vent cup, the discharge end of the wand is routed through the air-moving device, into the air distribution manifold and into the detection system.

PREFERRED EMBODIMENTS OF THE INVENTION

Figure 1:
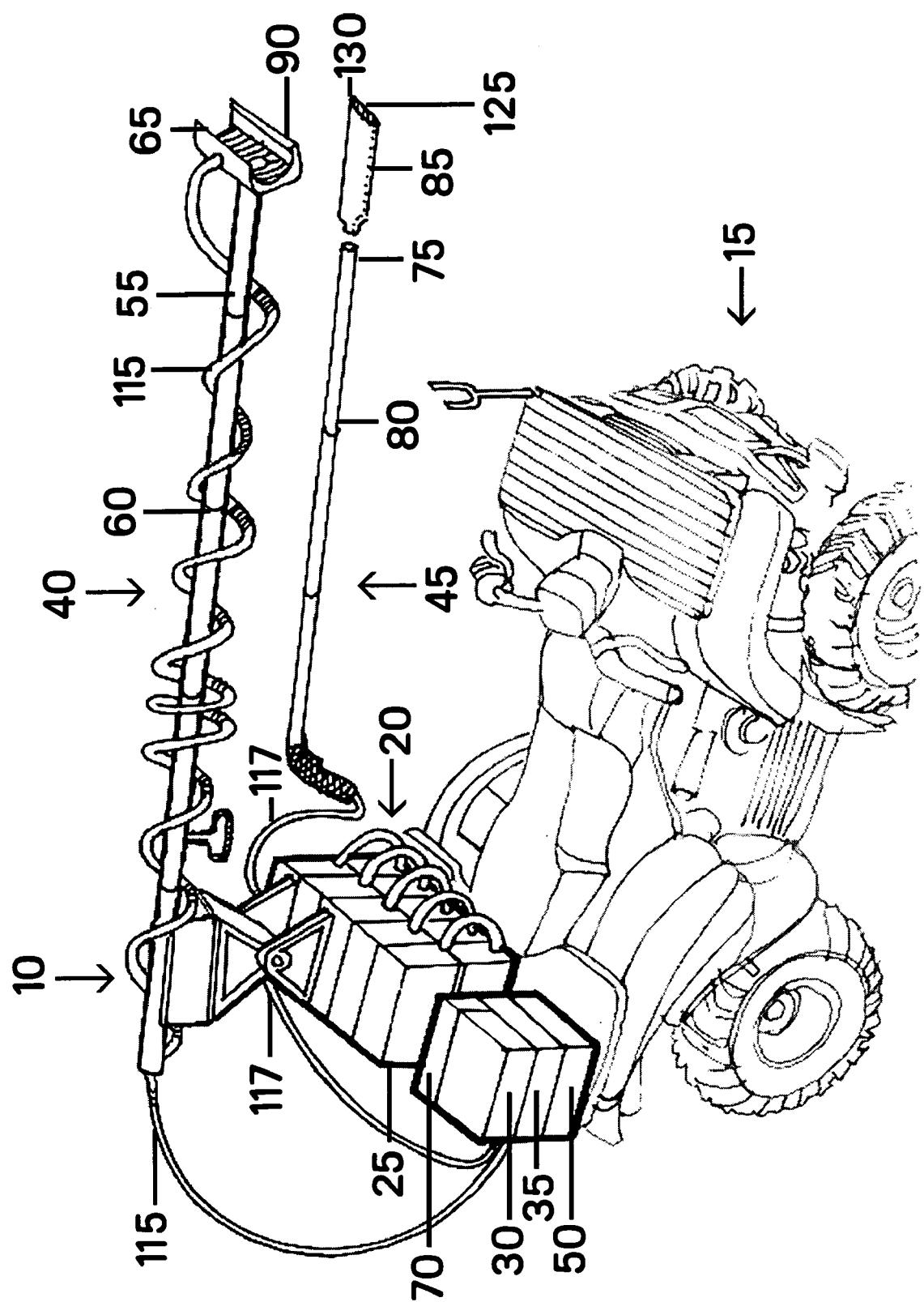
FIG. 1 illustrates one preferred embodiment of the present invention, featuring a mobile container inspection device mounted upon an all-terrain vehicle.

In the following detailed description of the preferred embodiments, reference is made to the accompanying drawings, which form a part hereof, and in which are shown by way of illustration specific embodiments in which the invention may be practiced. It is to be understood that other embodiments may be utilized and structural changes may be made without departing from the scope of the present invention. Like elements in the drawings will be represented by like numbers, and similar elements will be represented by like numbers with a different lower case letter suffix.

One preferred embodiment of the present invention is illustrated in FIG. 1. The detection system 10 is mounted upon an all-terrain vehicle (ATV) 15. Alternatively, the detection system 10 can be mounted upon any vehicle or trailer. The detection system 10 comprises a detector array 20, a detector array plenum 25, an air-moving device 30, a primary mover 35, a primary air sampling device 40, and a secondary air sampling device 45. The detection system 10 may be mounted up on the front or rear rack of the vehicle 15. The detection system 10 may draw power from the electrical system powering vehicle 15, or alternatively, a DC power supply 50, such as a battery pack, may also be mounted upon vehicle 15.

Considering the detection system 10 in more detail, primary air sampling device 40 is shown in its retracted configuration. Primary air sampling device 40 comprises a vent-mating end 55 mounted upon a telescoping actuator 60. The vent-mating end 55 is designed to mate with the standard vents installed upon various cargo containers, thus may be manufactured in various shapes and sizes. In the embodiment illustrated in FIG. 1, the vent-mating end 55 takes the form of a vent cup 65 that mates to a standard TC 104 container, thus has a generally rectangular shape. The telescoping actuator 60 is coupled to a control panel 70. Control panel 70 comprises automatic controls, which may include horizontal, vertical, extension and retraction controls, which move the primary air sampling device 40 into position to mate with the vent of a cargo container. Control panel 70 may also have manual controls.

In addition to the primary air sampling device 40, detection system 10 may also comprise a secondary air sampling device 45. Similar to primary air sampling device 40, the secondary air sampling device 45 comprises an air-sampling end 75 mounted upon a telescoping actuator 80. The telescoping action of the secondary air sampling device 45 is performed manually. The air sampling end 75 of secondary air sampling device 45 comprises a crevice tool attachment 85 that is capable of being placed adjacent to or inserted into cracks formed by the doors of the container, or any other apertures that may be present on the container or contained air space.

Figure 2:
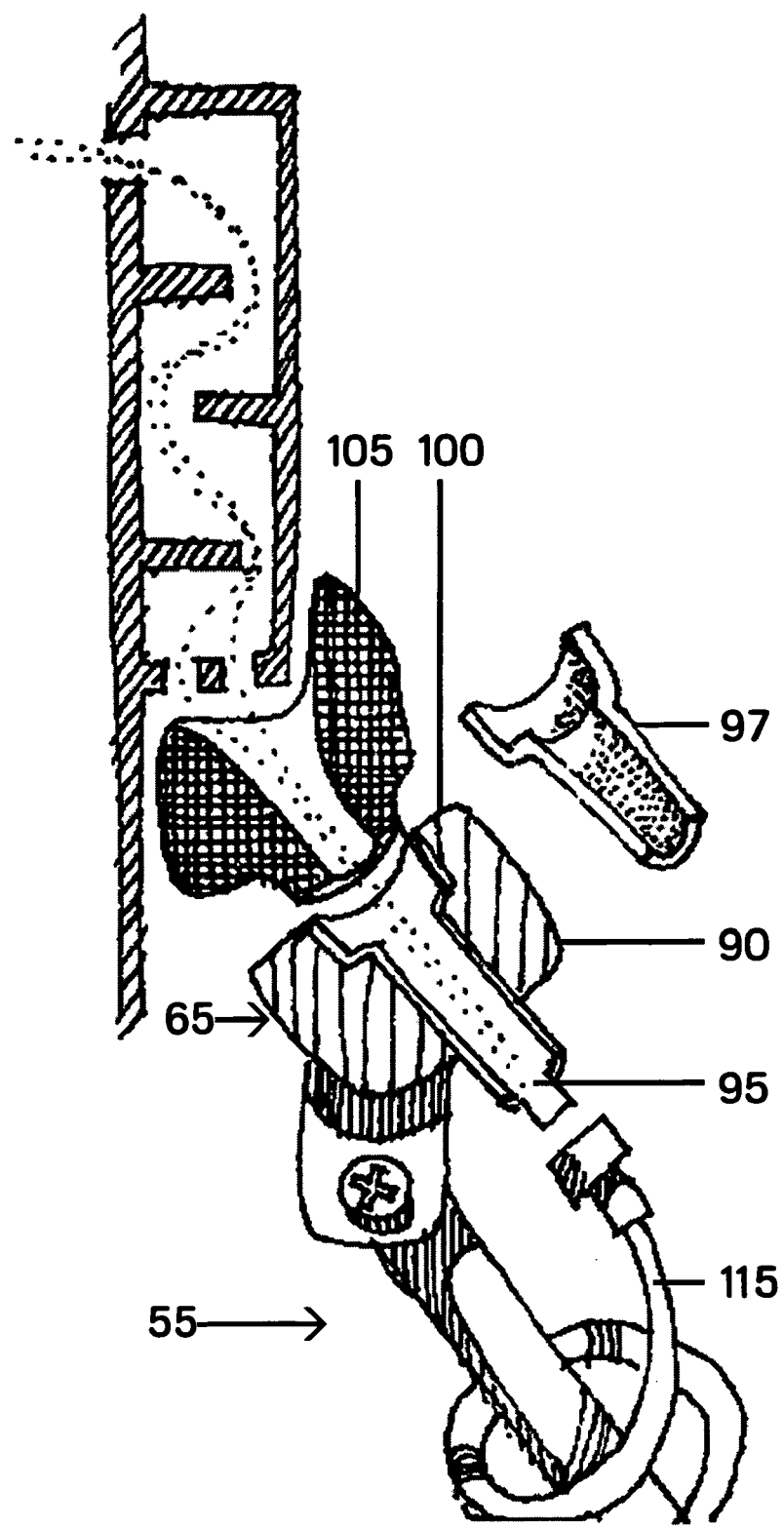
FIG. 2 illustrates one preferred embodiment of a vent cup for mating to a TC 104 container having a foam seal.

FIG. 2 illustrates the vent-mating end 55 of primary air sampling device 40 in more detail. In FIG. 2, the vent-mating end 55 takes the form of a vent cup 65 that mates to a standard TC 104 container, thus has a generally rectangular shape and dimensions slightly larger than the TC 104 vent. The vent cup 65 comprises an outer shell 90 defining an interior space 95 into which an air sample will be drawn. The vent cup 65 may also contain a replaceable insert 97 that fits within interior space 95 for ease of maintenance. The outer shell 90 has a leading edge 100 surrounding the interior space 95 that mates with sealing member 105 that communicates with the wall of the container being sampled. The sealing member 105 may be manufactured of a rubber or foam, or any other suitable pliable and conforming material, so that it conforms to any irregularities in the container wall.

Alternatively, the sealing member 105 may be in the form of an inflatable bladder, which can also conform the shape of the container wall. The inflatable bladder may utilize a separate connection to the air-moving device 30, such that air-moving device 30 may be employed to inflate and deflate inflatable bladder.

In addition, vent cup 65 may also comprise a radiological detection device, such as Geiger counters, ionization detectors, semiconductor diode detectors, scintillation counters, neutron detectors, or any other detector where proximity to the sample point is important.

Referring back to FIG. 1, the air sampling end 75 of the secondary air sampling device 45 comprises a crevice tool attachment 85. The leading edge 125 of crevice tool attachment 85 comprises a knife like portion 130 that can be used to pry open a crack between the container and a door or other aperture and to slide between any seal that may be present. Air duct 117 connects the secondary air sampling device 45 to air-moving device 30.

The outer shell 90 of the vent cup 65 also comprises an air duct 115 that connects the vent cup 65 to the air-moving device 30, such as a vacuum pump, air compressor, or similar device, which pulls air from within the container into the vent cup 65 and through the air duct 115. Air moving device 30 is powered by primary mover 35, which is preferably a standard squirrel cage induction motor. If the inflatable bladder is used as the sealing member 105, primary mover 35 may be a reversible motor such that the air-moving device 30 can be employed to inflate the bladder as necessary.

The air duct 115 connecting the vent cup 65 to the air-moving device 30 travels along the length of the telescoping actuator 60 holding the vent cup 65 and terminates at the air-moving device 30, which discharges into detector array plenum 25. Detector array plenum 25 is coupled to detection array 20, which comprises a plurality of individual detectors capable of detecting chemical and high-explosive agents, biological agents, radiological agents, and nuclear material, as well as other types of contraband such as illegal substances, embargoed material or stowaways. Detector plenum 25 may be designed to feed each of the plurality of individual detectors concurrently or, alternatively, detector plenum 25 may comprise a valving arrangement that permits the user to select which detectors are to be utilized for a particular air sample.

Considering the detector array 20 in more detail, the array may house any sensor capable of detecting chemical and high-explosive agents, biological agents, radiological agents, and nuclear material, as well as other types of contraband such as illegal substances, embargoed material or stowaways. The, sensors could include the Joint Biological Point Detection System (JBPDS) manufactured by Intellitec of Jacksonville, Fla., designed to detect and identify a plurality of biological pathogens. The sensors may also include other similar types of fully-integrated, detecting and identifying biological agent sensors, utilizing automated immunoassay methods, that include the 4WARN manufactured by General Dynamics Canada of Calgary, AB, Canada; Portal Shield or JBREWS manufactured by Sentel of Alexandria, Va.; or others. Some sensors could also take the form of a PCR-Nucleic Analysis system such as those manufactured by Cepheid of Sunnyvale, Calif., or Idaho Technologies of Salt Lake City, Utah. Some sensors could also take the form of detectors that serve only to detect the presence of biological material in particles in the analyzed air stream, like the BIONI, manufactured by Pacific Scientific Instruments of Grant's Pass, Oreg.; the Biological Aerosol Warning System Tier III developed by MIT Lincoln Laboratories in MA; the UV-APS, manufactured by TSI Inc. of St. Paul, Minn.; the UV-FLAPS and BARTS manufactured by General Dynamics Canada of Calgary, AB, Canada; or others. The sensors could also include a particle detector based system like the Biological Aerosol Warning System Tier I, manufactured by Lockheed Martin of Manassas, Va.

In addition, a simple collector, such as a filter or a BioCapture system manufactured by Mesosystems, Inc of Kennewick, Wash.; or other type of particle capture device could also be part of the sensor suite. Such a unit would be intended to capture particles for later laboratory analyses including culturing, immunoassay, and PCR-nucleic acid methods. Such a unit would also be useful for forensic purposes and for the collection of evidence. The sensor suite could also include one or more chemical warfare agent sensors such as ion mobility spectrometers including the ChemPro 100 or the M-90 manufactured by Environics Oy of Mikkeli, Finland, or similar sensors manufactured by Graseby Ionicics and ETG; surface acoustic wave sensor based devices including the JCAD sensor, manufactured by BAE Systems of San Antonio, Tex.; the HAZMATCAD, manufactured by Microsensor Systems Inc. of Bowling Green, Ky.; the Micro Chem Lab on a Chip manufactured by Sandia National Laboratories in Albuquerque, N. Mex.; the SnifferSTAR sensor manufactured by Lockheed Martin of Manassas, Va. and Sandia National Laboratories, or others. They could also take the form of explosives sensors, such as those manufactured by Ion Track Instruments of MA or Smith's Sensors of NJ (formerly Barringer), or contraband drugs sensors manufactured by the latter two manufacturers. The sensors could also include sensors for radiological particles in air, including Geiger counters and other radiological detectors, such as broad beam single scintillation detectors, narrow beam single scintillation detectors, dual scintillation detectors and neutron detector arrays.

In addition to the plurality of detectors housed within detector array 20, the array 20 would also include a means to communicate the readings from the components of the detection array 20 to the user, such as an audible alarm system or an on-board computer that displays the results gathered from the various detector components.

Figure 3:
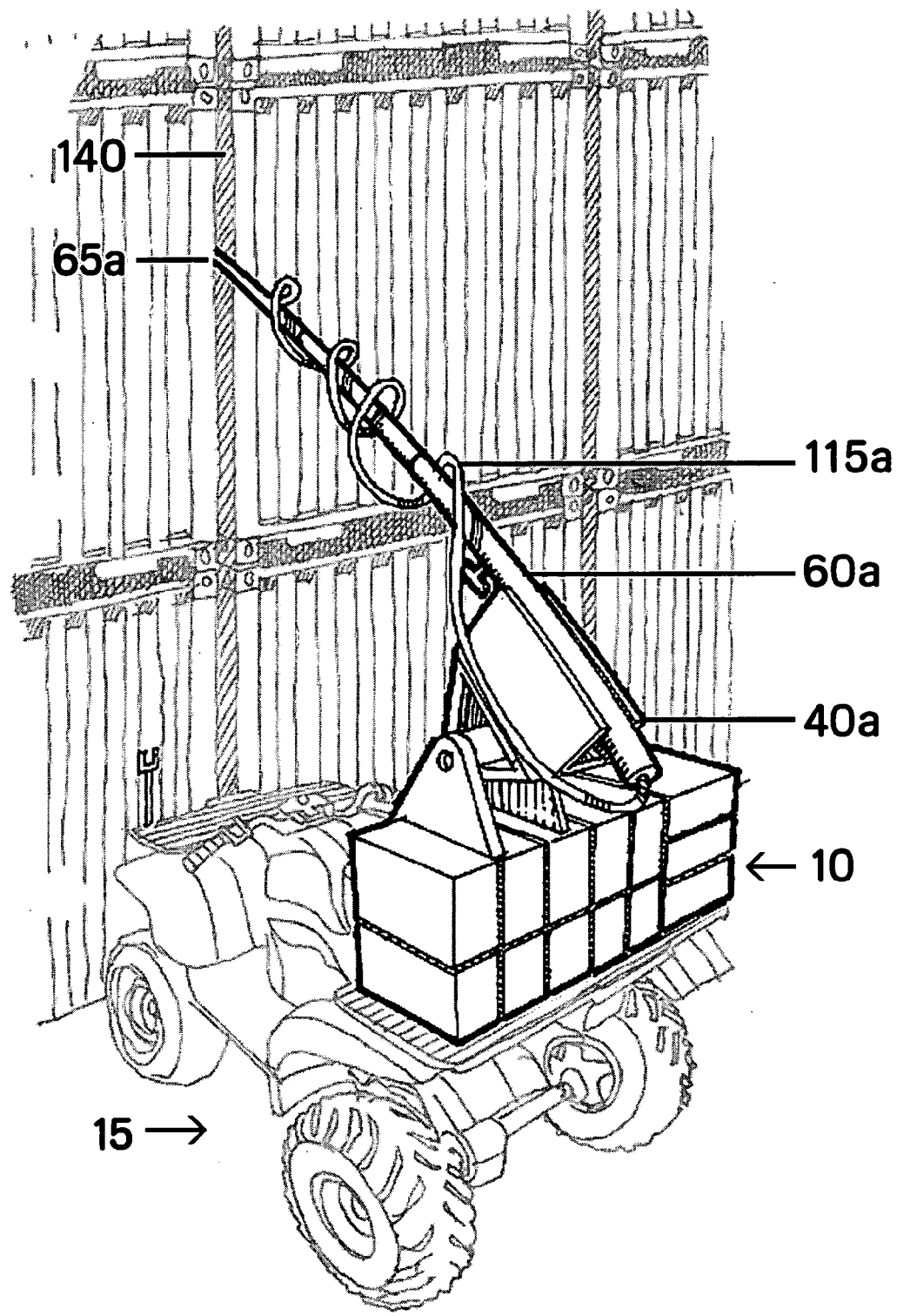
FIG. 3 illustrates one preferred embodiment of the present invention, featuring a mobile container inspection device mounted upon an all-terrain vehicle employing a crevice tool to take an air sample.

As shown in FIG. 3, the entire detection system 10 is mounted upon a vehicle 15, which can be placed within close proximity to a container 140 while it is in storage or while it is in place upon the vessel, truck, plane, or railcar on which it was shipped. FIG. 3 illustrates the use of the detection system 10 to sample the air within a standard TC 104 container 140 when containers are stacked in close proximity. The air sampling device 40a has been fitted with a crevice tool attachment 85a (not shown). The user pilots the vehicle 15 within close proximity to the container 140 and utilizes the automatic controls 70 to extend the telescoping actuator 60a into position. The crevice tool attachment 85a is positioned between containers and may be located adjacent to the vent container 140 or adjacent to or inserted in a crack in the container wall. The primary mover 35 is engaged and air-moving device 30 begins to pull air from within container 140 through air duct 115a, and into detector array plenum 25 and detector array 20.

Figure 4:
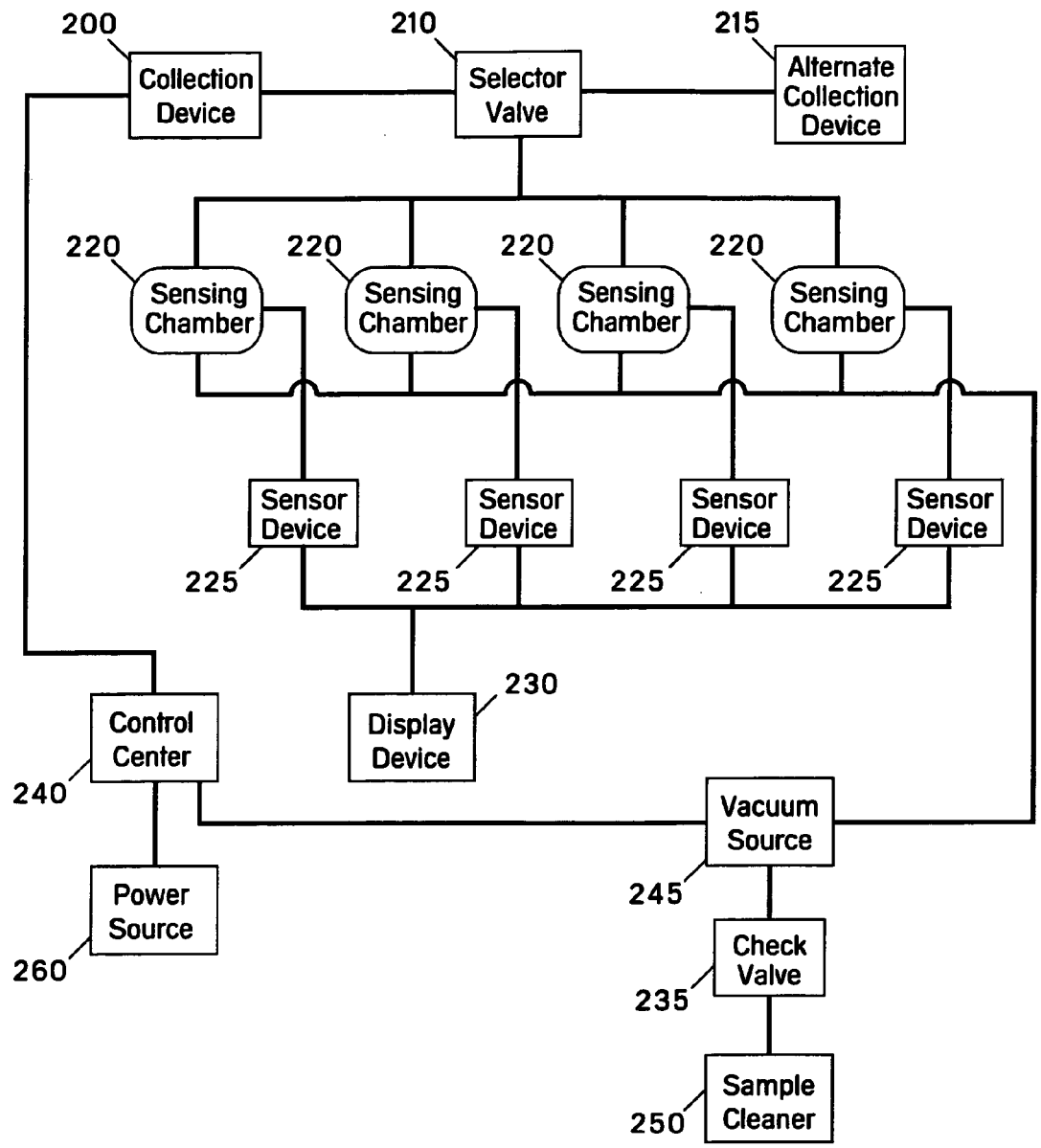
FIG. 4 is a schematic diagram of one preferred embodiment of the detector array and peripheral equipment.

FIG. 4 presents a schematic diagram of one preferred embodiment of the present invention. An air sample is collected with either collection device 200 or alternate collection device 215, which may be either the vent cup mounted upon the telescoping actuator or the crevice tool mounted upon the manual sample collecting device as described above. The sample is collected by engaging vacuum source 254, which may be a compressor, vacuum pump, or the like, which reduces the system pressure below atmospheric pressure and causes the air sample to be drawn into the appropriate collection device. Selector valve 210 is positioned with the flow stream between collection device 200 and alternate collection device 215 such that either collection device 200, 215 is individually operable. From selector valve 210, the air sample proceeds through a distribution manifold (not shown) and into a plurality of sensing chambers 220 for the detection of chemical, biological, radiological, nuclear, high explosive threats, as well as other types of contraband, including illegal substances, embargoed materials, hazardous industrial materials, chemical vapor or material, and human occupancy of the container. Each sensing chamber 220 is coupled to conventional electronic sensor output devices 225 that will provide the results of the analyses for each sensing chamber 220. The sensor output devices 225 are coupled to display device 230, which may be an on-board computer and/or printer. The control center 240 provides controls for all electrical and mechanical devices, which are supplied power via power source 260.

After the air sample is analyzed in sensing chambers 220, the air sample completes its flow stream by discharging from vacuum source 245. A check valve 235 in the discharge prevents backflow into the detection system. After being discharged, the air sample may be filtered, combusted, and/or scrubbed in device 250 to prevent contaminated air from being discharged into the environment.

Although the present invention has been described in terms of specific embodiments, it is anticipated that alterations and modifications thereof will no doubt become apparent to those skilled in the art and having the benefit of this disclosure. It is therefore intended that the following claims be interpreted as covering all alterations and modifications that fall within the true spirit and scope of the invention.

What is claimed is:

1. A portable inspection apparatus for sampling air within a container and contemporaneously analyzing the sampled air for detection of a plurality of different security threats, said apparatus comprising:

a vent cup for withdrawing an air sample from within a container through a container vent having one or more openings, wherein the vent cup comprises a housing that fits over the one or more openings in the container vent, and the housing is mounted upon a telescoping arm that is positioned with a control mechanism;

an air-moving device having a suction port and a discharge port;

a conduit connecting the vent cup to the suction port of the air moving device such that when the air moving device is operating, air is pulled into the vent cup from the container; and an air distribution manifold connected to the discharge port of the air moving device for receiving the air sample and distributing the air sample to a plurality of sensors, wherein each of the plurality of sensors is adapted for contemporaneously detecting a different security threat during withdrawal of the air sample from within the container.

2. The portable inspection apparatus of claim 1, wherein the portable inspection apparatus is mobile.

3. The portable inspection apparatus of claim 2, wherein the portable inspection apparatus is mounted on a vehicle selected from the group consisting of a truck, a car, an all terrain vehicle (ATV), a wagon, and a cart.

4. The portable inspection apparatus of claim 3, wherein the vehicle provides power to the mobile inspection apparatus.

5. The portable inspection apparatus of claim 2, further comprising a DC power supply for a supplying power to the mobile inspection apparatus.

6. The portable inspection apparatus of claim 1, wherein the housing further comprises a sealing member connected to the housing and disposed between the housing and the container.

7. The portable inspection apparatus of claim 1, wherein the plurality of sensors are selected from the group consisting of sensors for sensing chemical, biological, radiological, nuclear, and high-explosive materials.

8. The portable inspection apparatus of claim 1, wherein the plurality of sensors are selected from the group consisting of sensors for sensing illicit drugs, hazardous industrial materials, and chemical vapors and materials.

9. The portable inspection apparatus of claim 1, wherein at least one of the plurality of sensors senses the presence of human occupancy within the container.

10. A method for withdrawing an air sample from within a container having a closed aperture with a door defining a small space between the door of the closed aperture and the container wall and contemporaneously analyzing the air sample for a plurality of different security threats, the method comprising the steps of:

providing a portable inspection apparatus comprising an air sampling device having a telescoping arm mounted crevice tool for withdrawing an air sample from within the container, an air-moving device having a suction port and a discharge port, a conduit connecting the air sampling device to the suction port of the air-moving device such that when the air-moving device is operating, the air sample from the container is pulled into the air sampling device through the crevice tool and into an air distribution manifold, wherein the air distribution manifold is connected to the discharge port of the air-moving device for receiving the air sample and distributing the air sample to a plurality of sensors;

positioning with a control mechanism the telescoping arm mounted crevice tool within the small space between the door of the closed aperture and the container wall;

operating the air-moving device to withdraw the air sample from the container and to discharge the air sample into the air distribution manifold; and having the air sample from the air distribution manifold analyzed contemporaneously for a plurality of different security threats by the plurality of sensors.

11. The method of claim 10, wherein the portable inspection apparatus is mobile.

12. The method of claim 11, wherein the portable inspection apparatus is mounted on a vehicle selected from the group consisting of a truck, a car, an all terrain vehicle (ATV), a wagon, and a cart.

13. The method of claim 12, wherein the vehicle provides power to the portable inspection apparatus.

14. The method of claim 10, wherein the portable inspection apparatus further comprises a DC power supply for supplying power.

15. The method of claim 10, wherein the plurality of sensors are selected from the group consisting of sensors for sensing chemical, biological, radiological, nuclear, and high-explosive materials.

16. The method of claim 10, wherein the plurality of sensors are selected from the group consisting of sensors for sensing illicit drugs, hazardous industrial materials, and chemical vapors and materials.

17. The method of claim 10, wherein at least one of the plurality of sensors senses the presence of human occupancy within the container.

* * * * *